US010422795B2

(12) United States Patent
Chiang et al.

(10) Patent No.: US 10,422,795 B2
(45) Date of Patent: Sep. 24, 2019

(54) URINARY CRYSTAL DETECTION METHOD

(71) Applicant: NATIONAL YANG MING UNIVERSITY, Taipei (TW)

(72) Inventors: Hui-Hua Chiang, Taipei (TW); Chih-Chia Huang, Tainan (TW)

(73) Assignee: National Yang-Ming University, Taipei (TW)

(*) Notice: Subject to any disclaimer, the term of this patent is extended or adjusted under 35 U.S.C. 154(b) by 354 days.

(21) Appl. No.: 15/496,822

(22) Filed: Apr. 25, 2017

(65) Prior Publication Data
US 2017/0227534 A1 Aug. 10, 2017

Related U.S. Application Data

(63) Continuation-in-part of application No. 14/455,395, filed on Aug. 8, 2014, now abandoned.

(30) Foreign Application Priority Data

Jan. 20, 2014 (TW) .............................. 103101919 A

(51) Int. Cl.
*G01N 33/00* (2006.01)
*G01N 33/48* (2006.01)
*G01N 15/06* (2006.01)
*G01N 33/543* (2006.01)
*G01N 33/58* (2006.01)
*G01N 21/65* (2006.01)
*G01N 21/64* (2006.01)
*G01N 33/68* (2006.01)

(52) U.S. Cl.
CPC ... *G01N 33/54326* (2013.01); *G01N 21/6428* (2013.01); *G01N 21/65* (2013.01); *G01N 33/582* (2013.01); *G01N 33/6893* (2013.01); *G01N 2021/6417* (2013.01); *G01N 2800/345* (2013.01)

(58) Field of Classification Search
CPC ......... G01N 33/00; G01N 33/48; G01N 15/06
USPC .................................. 422/68.1, 73; 436/43
See application file for complete search history.

(56) References Cited

U.S. PATENT DOCUMENTS

| | | | |
|---|---|---|---|
| 6,620,627 B1 | 9/2003 | Liberti et al. | |
| 7,186,245 B1 * | 3/2007 | Cheng ...................... | A61F 5/44 604/349 |
| 7,208,134 B2 | 4/2007 | Bromberg et al. | |
| 8,486,720 B2 | 7/2013 | Banerjee et al. | |

(Continued)

OTHER PUBLICATIONS

Chen, Po-An., et al, Phosphorylate-terminated magnetic nanoparticles for efficient separation applied to urine crystals, *the Second International Conference on Materials, Science and Environments (ICMEE)* Aug. 8-9, 2013, Yokohama, Japan, 27 pages.

*Primary Examiner* — Brian J. Sines
(74) *Attorney, Agent, or Firm* — Muncy, Geissler, Olds & Lowe, P.C.

(57) ABSTRACT

The present invention provides an urinary crystal detection method, which is used with a crystal collecting unit and a crystal detecting unit. The method comprises steps of using magnetic particles to attach urinary crystals from a sample. Then, providing a magnetic field to separate the urinary crystals. Further to analyz their constituent by the Raman signals of the urinary crystal to access an urinary calculus result for urinary stone patient.

12 Claims, 12 Drawing Sheets

(56) References Cited

U.S. PATENT DOCUMENTS

| | | | |
|---|---|---|---|
| 2002/0098518 A1* | 7/2002 | Levinson | C12Q 1/18 |
| | | | 435/7.1 |
| 2003/0232388 A1 | 12/2003 | Kreimer et al. | |
| 2004/0185482 A1 | 9/2004 | Stuelpnagel et al. | |
| 2005/0233461 A1* | 10/2005 | Levinson | G01N 25/147 |
| | | | 436/79 |
| 2009/0136594 A1* | 5/2009 | McLeroy | A61B 17/221 |
| | | | 424/648 |
| 2015/0099704 A1* | 4/2015 | Rimer | C07K 7/08 |
| | | | 514/15.4 |
| 2015/0118688 A1 | 4/2015 | Weidemaier et al. | |

* cited by examiner

URINARY CRYSTAL DETECTION METHOD

CROSS-REFERENCE TO RELATED APPLICATIONS

This continue in part (CIP) application claims priority under 35 U.S.C. §119(a) on patent application Ser. No. 14/455,395 filed in U.S. Aug. 8, 2014, the entire contents of which are hereby incorporated by reference.

FIELD OF THE INVENTION

The invention relates to the urinary crystal detection method. Particularly, the urinary crystal detection method is used to distinguish the types of urinary calculus for patients in different urinary calculus.

BACKGROUND OF THE INVENTION

Urinary calculus is a common disease. The main components of normal urine are crystals and substances. The crystals can be calcium oxalate, calcium phosphate, uric acid, uric acid saline, cystine, xanthine and so on. When the dissolved concentration of crystal is saturation in the urine, it might appear to super-saturation. Then the dissolved crystals will precipitate and result in urinary calculus occurrence.

Traditionally, the urine sediment is used to detect different morphology of sediments. The urine sediment is using an optical microscope to further determine the types of the urinary crystals. The urine sediment is easy to make erroneous judgment cause of stereo structure and irregular shape of the crystals, and different faces of crystals may appear different physical forms. Determination of crystal types always depends on the experiences of the examiner, therefore it has largely humane errors caused different examiner may have different result. Briefly, the irregularly shaped crystals cannot be accurately determined by its appearance alone.

Because of the traditional detecting method is using a microscope to determine the type of the crystals, it takes much time to search the location of the urinary crystals in patients with less amount of crystals. The traditional detecting method might ignore most of urinary crystals because they are translucent. Moreover, the urine includes many substances such as proteins, cells, bacteria, and so on, these substances may interfere the determination. The patients may miss the opportunity for early treatment.

Currently, the urinary calculus detection is conducted by imaging methods, such as X-ray imaging system, urinary system imaging, computed tomography, ultrasound, etc. In addition, the composition of the urinary calculus can not be determined before acquiring the urine calculus.

Clinically, the urinary calculi is easy to recurin patients. It is very important to know the composition of urinary calculus. Furthermore the characterization of urinary calculi is also important for therapy and prevention purpose.

The analysis methods for urinary calculi are numerous, including X-ray imaging, chemical analysis, X-ray diffraction, infrared spectroscopy microscopy, scanning electron microscopy, chromatographic automatic analysis, thermal stress analysis, thin film polarizers microscopy and so on. Currently, the urinary calculus can only be acquired through surgery or from the extracorporeal shock wave procedure. The types of urinary calculus can only be analyzed after acquiring the urinary calculus sample.

Recently, some researches have demonstrated that there is a strong correlation between the composition of the urinary calculus and the type of urinary crystal in the urinary calculus patients. Therefore, the successful and reliable identification of the type of urinary crystal in the patients having urinary calculus plays an important role in the treatment or therapy of urinary calculus.

So far, people still have the problems in detection and analysis of urinary crystals. The traditional urinary crystals detecting method (relying examiner's visual observation under the microscope) is inconvenient and may cause erroneous result, and cannot directly and accurately determine the type the crystals to make therapeutic decisions.

The above visual observation method has its limitation, more importantly, it still cannot accurately and efficiently determine the types of urinary crystal. The present invention can efficiently collect and accurately determine the types of urinary crystals.

SUMMARY OF THE INVENTION

The present invention provides a method, which is used with a urinary crystal detection system, can collect and detect urinary crystals from patients' urine samples, and further determine the types of urinary crystals. The type of the urinary crystal is closely related to the type of the urinary calculus, so the patients can have different treatments according to different types of the urinary crystals.

The urinary crystal detection system includes a crystal collecting unit and a crystal detecting unit. The crystal collecting unit includes a magnetic separating device.

The crystal collecting unit is used to receive an urine sample which is added plurality of magnetic particles. The magnetic particles will absorb the urinary crystals in the sample. The adsorbed magnetic particles will assist to collect and dispose on a carrier when the magnetic separation device produces a magnetic field. The crystal detecting unit receives the carrier and determines the type of the urinary crystals.

In an embodiment of the invention, the magnetic separating device can be a magnet or a magnetite, which is not limited herein. All devices can provide magnetic fields are the scope in this invention.

Further, in an embodiment of the invention, the urinary crystal detection system include a sample processing unit for pretreatment the urine sample, the crystal collecting unit for collecting the crystals by magnetic method, and the crystal detecting unit.

The above sample processing unit comprises a pH detecting device and pH processing device. The pH detecting device measures the pH value of the urine sample. The pH processing device performs acid or alkali treatment according to the detected pH value.

The crystal detecting unit can be any detector, such as a microscopy, a Raman spectroscopy, an infrared spectroscopy, a fluorescence spectroscopy, a X-ray diffraction (XRD) or image analyzer, which is not limited herein.

In an embodiment of the invention, the crystal detecting unit is a Raman spectroscopy which can obtain optical Raman scattering signals from urinary crystal and further to determine the type of the urinary crystals.

Moreover, the crystal detecting unit comprises a signal analyzing device which including a database, wherein the database use to receive the Raman signals to analyze and compare. The database contains all kinds of standard Raman signals of urinary crystal, as well as the urinary calculi correspond to the type.

Otherwise, the present invention provides an urinary crystal detection method, the steps are as following:

First, providing a urine sample from a patient. Second, adding a plurality of magnetic particles into the urine sample, the magnetic particles attaching to a plurality of urine crystals of the urine sample. Third, providing a magnetic field to the urine sample. Then, the magnetic field attracts and collects the urinary crystals which are absorbed by the magnetic particles. Finally, analyzing and comparing the types of urinary crystals with a component information from a database to receive a result of the urinary calculus.

In an embodiment of the invention, before adding plurality of magnetic particles to the urine sample, the urine sample is performed by a pretreatment step. The pretreatment step comprises detecting the pH value of the urinary sample and performing acid or alkali processes according to the pH value. If the pH value of urinary sample is less than 7, the urinary sample is executed the acid processes, and if the pH value of urinary sample is more than 7, the urinary sample is executed the alkali processes. Both processes are used to separate the proteins, cells and etc. from urinary crystals. The acid processes using 5%~15% acetic acid added to the urinary sample, the alkali processes using 5%~15% NaOH added to the urinary sample and both of which is not limited herein.

The method is used to detect the type of the urinary crystals comprises microscopy analysis, Raman spectroscopy, infrared spectroscopy, fluorescence spectroscopy, or X-ray diffraction, which is not limited herein.

In an embodiment of the invention, a microscopic Raman spectroscopy unit is used to analyze a Raman signal of the urinary crystals, and comparing the peak characteristics of the Raman signal with a component information from a database, wherein the component information is a plurality of reference peak characteristics from different urinary crystals related to a plurality of urinary calculus. It can receive a result of the urinary calculus which the reference peak characteristics is similar as the Raman signal.

In another embodiment, a fluorescence spectroscopy unit is used to analyze an auto-fluorescence signal of the urinary crystals.

Moreover, the present invention also provides a magnetic particle containing a core, a protective layer and a functional group. The protective layer covers the core. The functional group is modified on the surface of the protective layer, and the functional group is $PO_4^{3-}$, fluorescent molecules or the combination thereof.

In an embodiment of the invention, the components of the cores can be Fe, Co, Ni, $FeO_2$, $Fe_2O_3$ or $Fe_3O_4$. The components of the protective layers can be a surfactant, a polymer layer, PSMA, a co-polymer layer, a carbon/silica inorganic layer, collagen or gelatin. In a preferred embodiment, the component of the cores of the magnetic particles is $Fe_3O_4$ coated with gelatin as the protective layer, which is not limited herein. Furthermore, in a preferred embodiment, when the protective layer is the gelatin and the fluorescent molecule is FITC. Moreover, in a preferred embodiment, the size of the magnetic particles is 5-200 nm, which is also not limited herein.

In an embodiment, the component of the protective layer can be collagen or gelatin. The collagen or the gelatin contains most kinds of amino acid which can chemically and physically adsorb most kinds of urinary crystals. The collagen or the gelatin also contains the benzene ring structure which can physically adsorb the urinary crystals including uric acid. In specific type of urinary crystal, the functional group at the surface of the magnetic particles surface can be further modified. For example, the surfaces of the magnetic particles are modified by $PO(OH)_2$ or $PO_4^{3-}$ molecules which can attract Ca- and Mg-based urinary crystals with $Ca^{2+}$ or $Mg^{2+}$.

In another embodiment, the protective layer of the magnetic particle can be PSMA and can be modified by $PO(OH)_2$ or $PO_4^{3-}$, fluorescent molecules or the combination of the above. After adsorbing Ca-urinary crystals, the magnetic particles modified by fluorescent molecules can mark the Ca-urinary crystals. It is beneficial to quickly observe the location of the urinary crystals under the fluorescent microscope and it also can be used for automated detecting apparatuses. The automated detecting apparatuses can detect the urinary crystals via the fluorescent molecules. In a preferred embodiment, the fluorescent molecules are Pararosaniline hydrochloride (PAR), Crystal Violet (CV) or Fluorescein isothiocyanate (FITC).

The magnetic particles as tracer and collector described here can be applied to the urinary crystal detection system and method. According to the different urinary crystals, the magnetic particles can be modified by different functional groups, and these can be used selectively or combinatively in the urinary crystal detection system, which is not limited herein.

In sum, the urinary crystal detection system and method of the invention can efficiently collect and detect microcrystals in the urine. The urine of urinary calculus patients generally contains crystals. Magnetic nanoparticles is a magnetic target and an external magnetic field can be provided to separate urinary crystals/micro stones from other substances in urine. Types of urinary crystals can be determined by its Raman signals. Early detection can be achieved for urinary calculus patients, and it can detect whether there are micro stones or crystals or not. For emergency cases, if the patient has urinary calculus symptoms, this invention can also provide real-time diagnostic efficacy.

The invention has the advantages in assisting clinical examination to determine the crystals that may be hard to determine from its shape under the microscope (the original approach). The invention is more accurate, more specific, and can assist clinicians to determine individual treatment according to different types of urinary calculus, which can be determined from the type of urinary crystals. It is also convenient to keep tracking and monitoring the patients after urinary stone surgery and to reduce the relapse rate.

DETAILED DESCRIPTION OF THE INVENTION

For clarity of disclosure, and not by way of limitation, the detailed description of the invention is divided into the subsections that follow.

The present invention provides a method, which is used with a urinary crystal detection system, can collect and detect urinary crystals from patients' urine samples, so that different patients can have different treatments according to the types of the urinary calculus, which can be further determined from the type of the urinary crystal.

Figure 1:
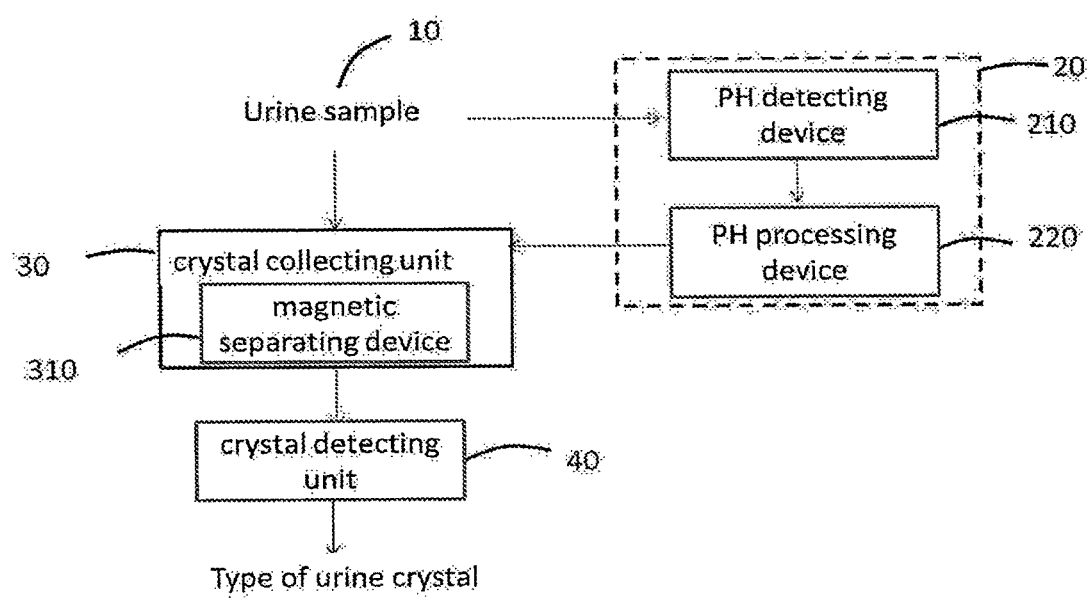
FIG. 1 is a diagram of the urinary crystal detection system in the invention.

Please refer to FIG. 1 showing a diagram of the urinary crystal detection system in the invention. The urinary crystal detection system includes a crystal collecting unit 30 and a crystal detecting unit 40. Also, the crystal collecting unit 30 includes a magnetic separating device 310.

An urine sample 10 of a patient is received by the crystal collecting unit 30, and is added magnetic particles. The magnetic separating device 310 attracts the magnetic particles attached to the urinary crystals, and disposes the magnetic particles and transfers the urinary crystals to a carrier, such as Slides, quartz slides and so on. The crystal detecting unit 40 detects the type of the urinary crystal.

The crystal detecting unit 40 can be a microscopy, a Raman spectroscopy, an infrared spectroscopy, a fluorescence spectroscopy, a X-ray diffraction (XRD) or image analyzer, which is not limited herein. In a preferred embodiment, the crystal detecting unit 40 is a Raman spectroscopy to measure Raman signals of the urinary crystals and further to determine the type of the urinary crystals.

The urinary crystal detection system also comprises a sample processing unit 20. The sample processing unit 20 including a pH detecting device 210 and pH processing device 220. The pH detecting device 210 measures the pH value of the urine sample 10. The urine sample 10 is detected by the pH detecting device 210 to generate a pH value, and executed processes by the pH processing device 220 according to the pH value. If the pH value of urine sample 10 is less than 7, the urine sample 10 is executed the acid processes; if the pH value of urine sample 10 is larger than 7, the urine sample 10 is executed the alkali processes. The acid processes and the alkali processes are used to separate the proteins, cells and etc. from the urinary crystals.

The urinary crystal detection system of the present invention can include or exclude the sample processing unit 20. The urine sample 10 can be directly used in the urinary crystal detection system of the present invention, or executed a pre-treatment by the sample processing unit 20 before the crystal collecting unit 30 receiving the urine sample 10. Moreover, a user can directly provide a pre-treated urine sample 10 for the urinary crystal detection system of the present invention, which is not limited herein.

Figure 2:
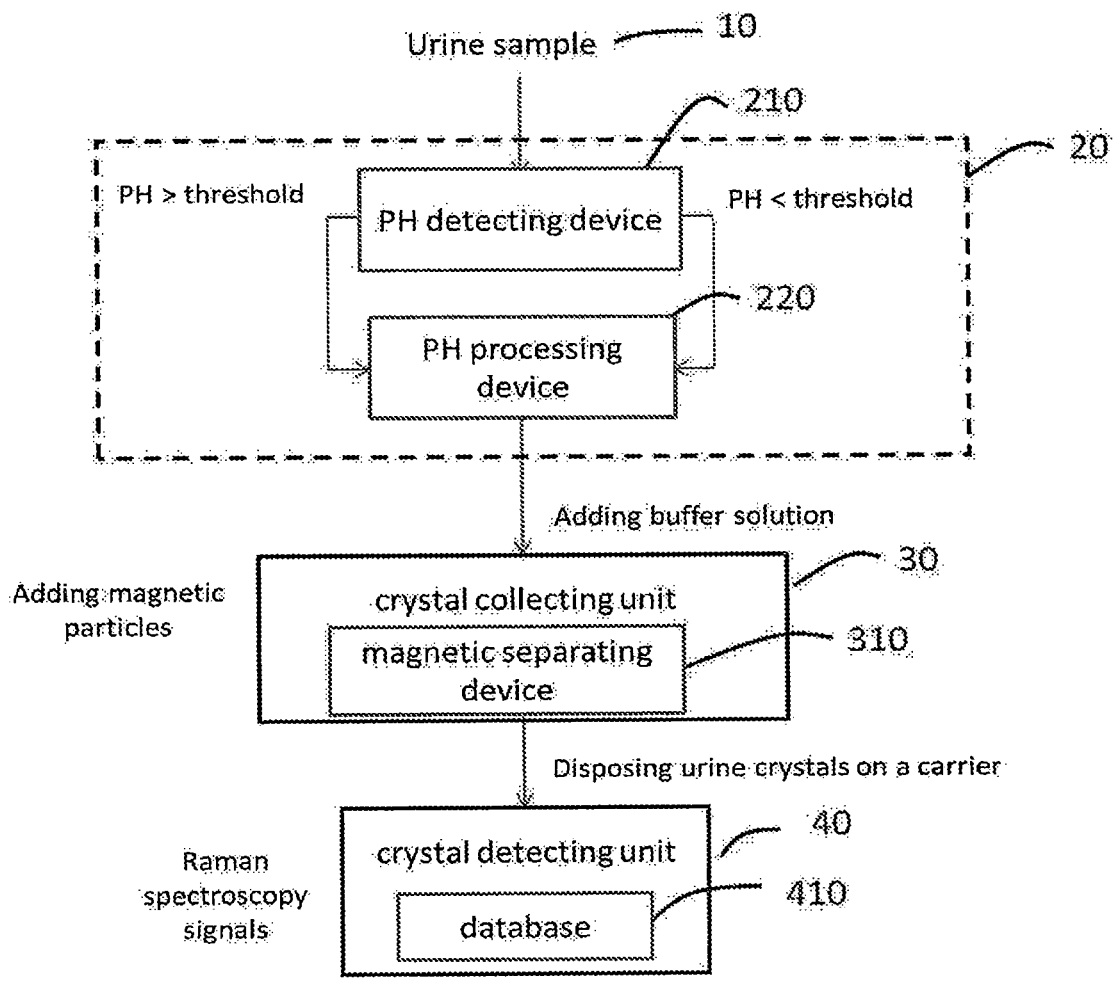
FIG. 2 is an embodiment diagram of the urinary crystal detection system in the invention.

Please refer to FIG. 2 showing a diagram of another embodiment of the urinary crystal detection system in the invention. The urine sample 10 is detected by the pH detecting device 210 to generate a pH value, and executed processes according to the pH value. The amount of the urine sample 10 is 1-5 ml from a patient's urine, which is not limited herein.

In an embodiment, when the pH value of the urine sample 10 detected is larger than a threshold, the urine sample 10 is added alkali solution. For example, the pH value of the threshold pH=7, the pH value from urine sample 10 detected is larger than 7, the urine sample 10 is added 5%~15% NaOH. In a preferred embodiment, the weight percentage concentration of NaOH is 10%, and the volume of NaOH is 200 µl, which is not limited herein.

In an embodiment, when the pH value from the urine sample 10 is lower than a threshold, the urine sample 10 is added acid solution. For example, the pH value of the threshold is 7, the pH value from the urine sample 10 is lower than 7, the urine sample 10 is added 5%~15% acetic acid. In a preferred embodiment, the weight percentage concentration of acetic acid is 10%, and the volume of acetic acid is 200 µl, which is not limited herein.

The criteria of the pH value of the threshold can be adjusted by users. The value of pH=7 is an example in the invention, but not limited herein.

In an embodiment, after the urine sample 10 is executed above-mentioned acid or alkali processes, the urine sample 10 containing urinary crystals is added buffer solution, such as adding 5 ml of secondary water or three-times distilled water, to clean and remove impurities, which is not limited herein.

Then, the urinary crystals from urine sample 10 are received by the crystal collecting unit 30. In an embodiment, a plurality of magnetic particles are added to the urine sample 10, and the magnetic particles adsorb onto urinary crystals. The magnetic separating device 310 attracts the magnetic particles to collect the urinary crystals adsorbed by the magnetic particles. The collected magnetic particles and the urinary crystals are disposed on a carrier, such as slides, quartz slides and so on.

The magnetic separating device 310 disposes the urinary crystals on the carrier, such as quartz slides. The carrier is received by the crystal detecting unit 40 to execute detecting processes. The crystal detecting unit 40 can be any detector, such as a microscopy, a Raman spectroscopy, an infrared spectroscopy, a X-ray diffraction (XRD) or image analyzer, which is not limited herein. In a preferred embodiment, the crystal detecting unit 40 is a Raman spectroscopy to measure Raman signals from urinary crystals, which is not limited herein.

The crystal detecting unit 40 comprise a database 410. The database 410 is used to store the component information of all kinds of urinary crystal and urinary calculus. The urinary crystal is detected by the crystal detecting unit 40 to generate a detecting result. The detecting result is compared with the database 410 to determine the type of the urinary crystal. In a preferred embodiment, the crystal detecting unit 40 is a Raman spectroscopy to measure the Raman signals of the urinary crystals. The peak characteristics of Raman signals are compared with the component information of the database 410 and further to determine the type of the urinary crystals, which is not limited herein.

Figure 3A:
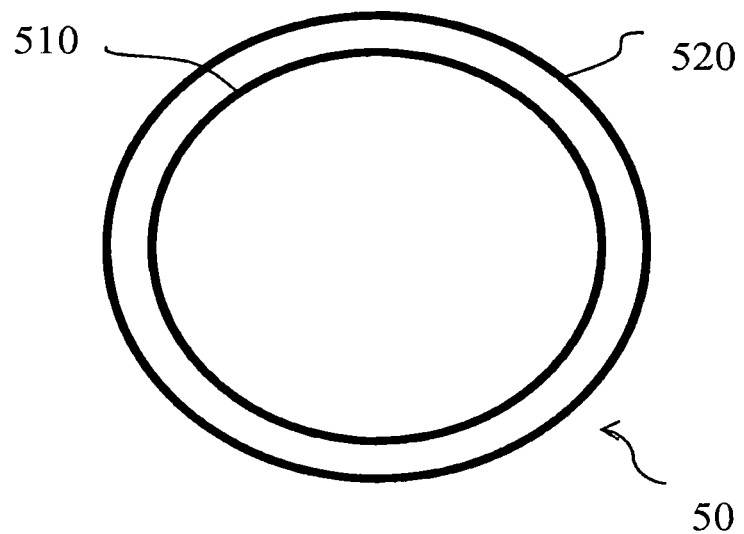
FIG. 3A is a diagram of the magnetic particles in the invention.

In an embodiment, the magnetic particles 50 are formed by a plurality of core 510 coated with protective layers 520. Please refer to FIG. 3A showing a diagram of the magnetic particle in the invention. The components of the cores 510 can be Fe, Co, Ni, $FeO_2$, $Fe_2O_3$ or $Fe_3O_4$, which is not limited herein. The components of the protective layers 520 can be a surfactant, a polymer layer, a carbon/silicon inorganic layer, collagen or gelatin. In a preferred embodiment, the component of the cores 510 of the magnetic particles 50 is $Fe_3O_4$ coated with gelatin as the protective layer 520. In a preferred embodiment, the component of the cores 510 of the magnetic particles 50 is $Fe_3O_4$ coated with PSMA as the protective layer 520, which is not limited herein.

The synthesis methods of the magnetic particles including coprecipitation method, thermal-chemical-vapor-deposition method, reduction method, micellar method, hydrothermal method and so on. Various synthetic methods are studied by scholars, which is not limited herein.

The main components of urinary calculi are calcium, magnesium, uric acid (such as calcium oxalate, magnesium ammonium phosphate). In a preferred embodiment, the magnetic particles 50 is $Fe_3O_4$ coated with gelatin (containing a benzene ring), and the component of the gelatin is animal collagen, which is a kind of natural high molecular polypeptide polymer. Therefore, the protective layer 520 composed of gelatin as magnetic particles 50 can absorb most kinds of urinary crystals. In a situation of adsorbing a specific type of urinary crystal, the surface of the magnetic particles 50 can be further modified a functional group to make the magnetic particles 50 can select types of urinary crystal, such as shown in FIG. 3B.

In another embodiment of the invention, the component of the cores 510 of the magnetic particles 50 is $Fe_3O_4$ coated with PSMA or gelatin as the protective layer 520. The PSMA includes benzene ring structure to adsorb most kinds of organic urinary crystals, such as adsorbing uric acid crystals, but which is not limited herein.

Figure 3B:
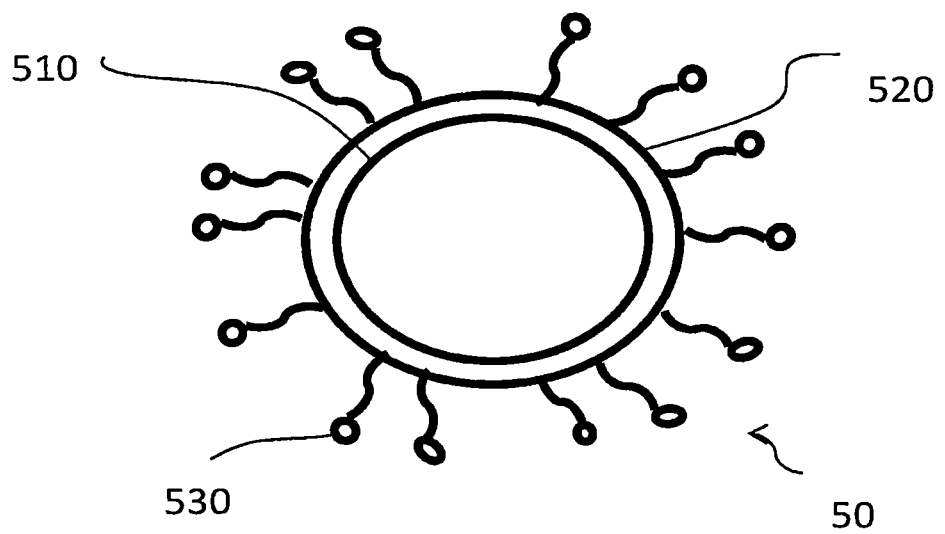
FIG. 3B shows an embodiment diagram of the magnetic particles in the invention.

In an embodiment of the invention, the magnetic particles 50 are formed by $Fe_3O_4$ and coated with surface-modified $PO_4^{3-}$, as shown in FIG. 3B. The characteristic of R—$PO_4^{3-}$ molecule is easy to bind with calcium ions or magnesium ions, thus the functional group of R—$PO_4^{3-}$ have chemical bonding with the surfaces of magnetic nanoparticles of $Fe_3O_4$. The surfaces of nanoparticles with functional $PO_4^{3-}$ group can further to form a covalent bond with calcium and magnesium. That is, the molecular structure is easy to have chemical reaction and bind with urine acid molecules, and it is effective to separate and purify urinary crystals with calcium or magnesium. Another example of magnetic particles 50 coated with the gelatin which structure contain benzene ring-rich functional group and hydrogen bond can be used for the adsorption of organic urinary crystals, such as adsorption of uric acid crystals, which is not limited herein.

Figure 3C:
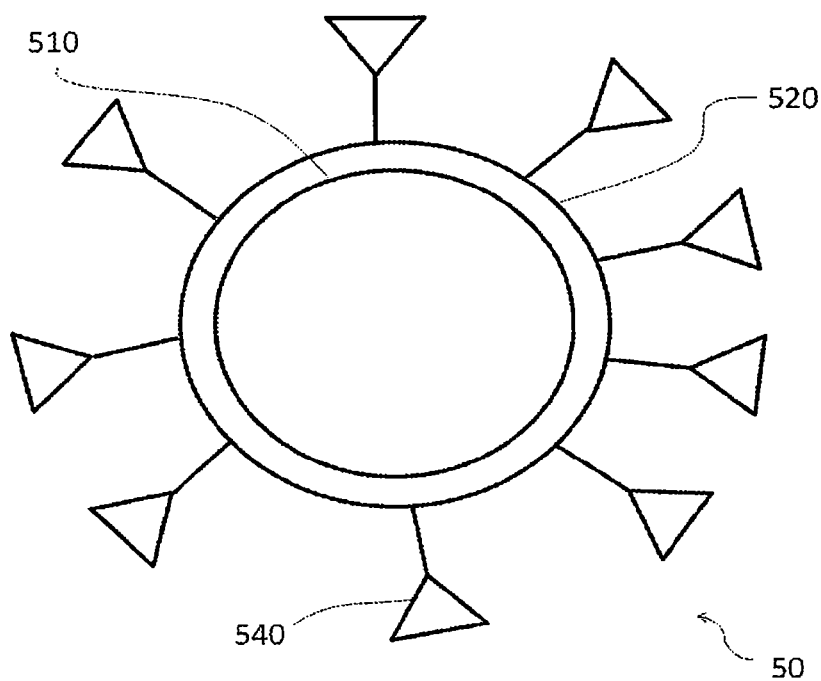
FIG. 3C shows a diagram of a third embodiment of the magnetic particle in the invention.

In another embodiment, the surfaces of the magnetic particles 50 are modified by fluorescent molecules 540, such as Pararosaniline hydrochloride (PAR), Crystal Violet (CV) or Fluorescein isothiocyanate (FITC), as shown in FIG. 3C. After adsorbing urinary crystals, the magnetic particles 50 modified by fluorescent molecules 540 can mark the uric acid crystals. It is beneficial to quickly and accurately detect the types of the urinary crystals and it also can be used for automated detecting apparatuses. The automated detecting apparatuses can detect the urinary crystals via the fluorescent molecules. Any component having a benzene ring structure, $NH_2$ functional group or fluorescent molecules with positive charge can be used, the present invention is not limited thereto.

Figure 3D:
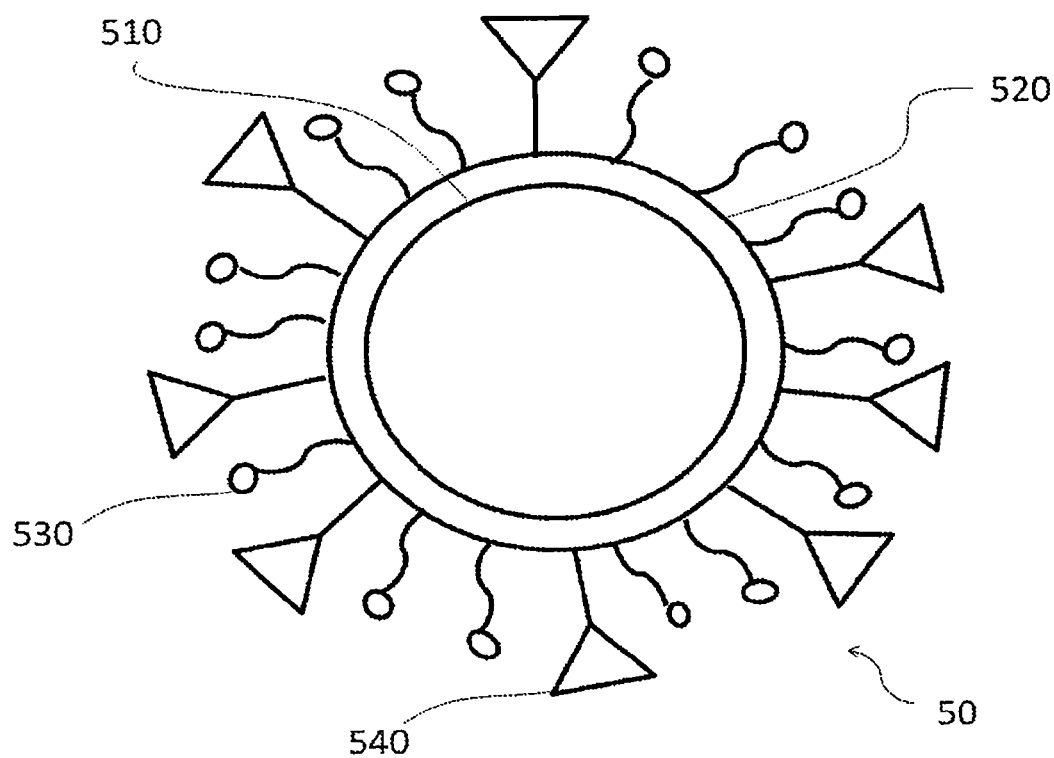
FIG. 3D shows a diagram of a fourth embodiment of the magnetic particle in the invention.

Furthermore, in an embodiment, in the FIG. 3D, the surfaces of the magnetic particles 50 can be modified by $PO_4^{3-}$ 530 and fluorescent molecules 540 at the same time to make the magnetic particles 50 can have the functions of determining types of the urinary crystals and marking the urinary crystals.

Figure 4A:
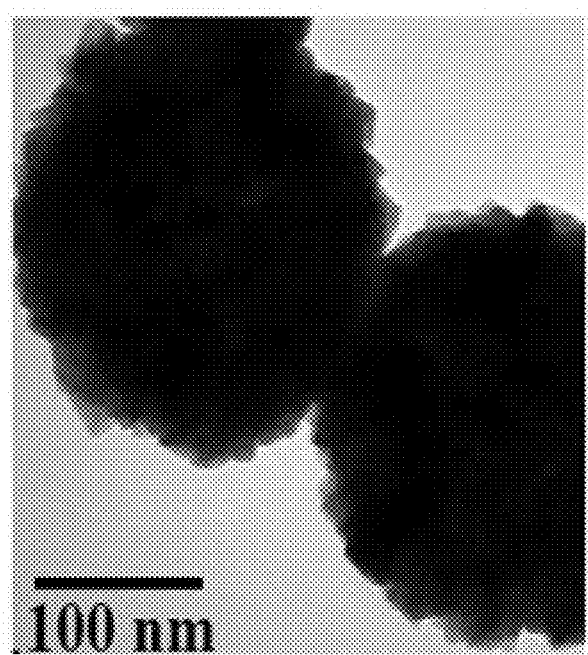
FIG. 4A shows an electron microscope diagram of the magnetic particles with the size of about 200 nm.
Figure 4B:
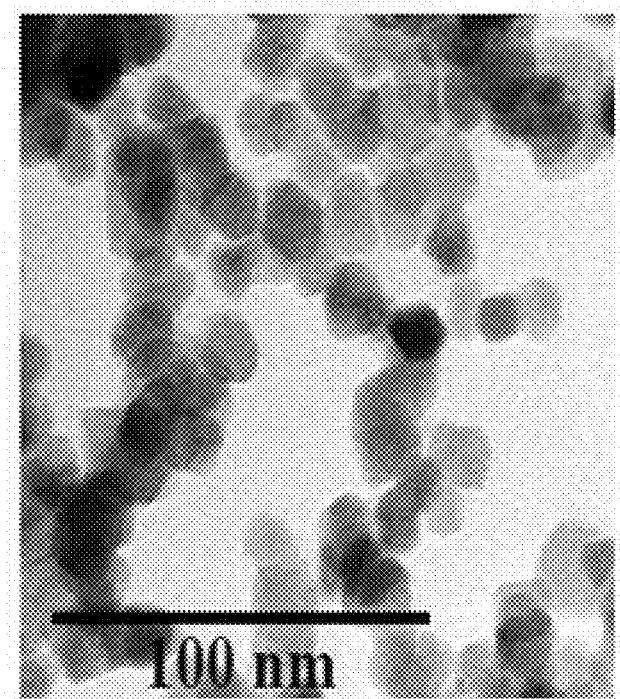
FIG. 4B shows an electron microscope diagram of the magnetic particles with the size of about 13 nm.

The size of magnetic particles is 5-200 nm, Please refers to FIG. 4A and FIG. 4B showing the electron microscope diagrams of different sizes of the magnetic particles. The size of magnetic particles in FIG. 4A is about 200 nm and the size of magnetic particles in FIG. 4B is about 13 nm. The preferred size of magnetic particle is 13 nm, which is not limited herein.

Figure 5A:
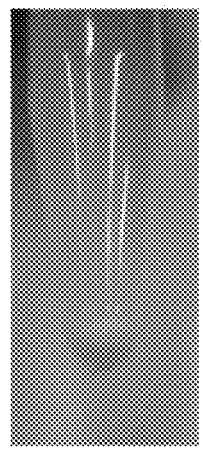
FIG. 5A is a diagram showing pure substance powder of Calcium oxalate.
Figure 5B:
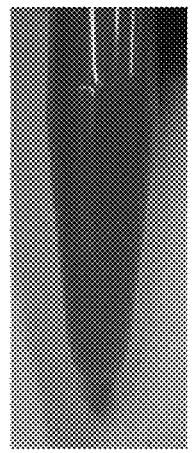
FIG. 5B is a diagram showing the magnetic particles formed by $Fe_3O_4$ added surface-modified. $PO_4^{3-}$. The magnetic particles are adsorbed onto the Calcium oxalate in urine.
Figure 5C:
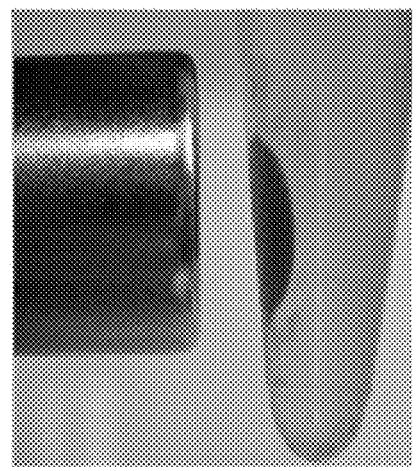
FIG. 5C is a diagram showing the magnetic particles and the adsorbed Calcium oxalate attracted by an external magnet.
Figure 6:
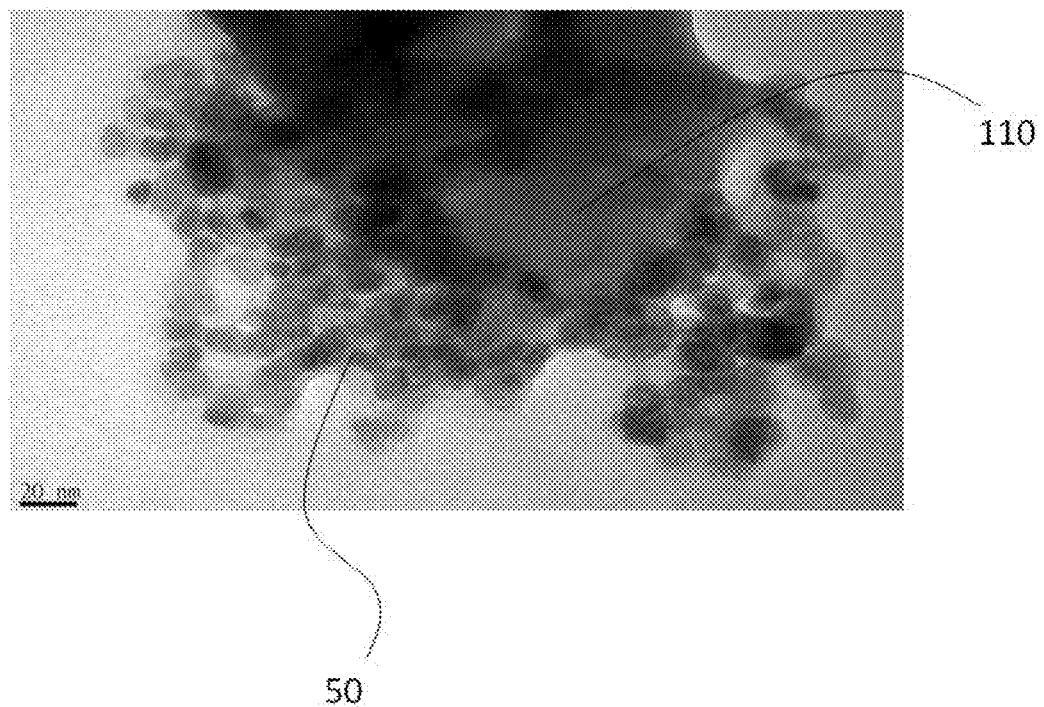
FIG. 6 shows a diagram of the magnetic particles adsorbed onto Calcium oxalate.

In above embodiment, please refer to FIG. 5A to FIG. 5C showing diagrams of surface-modified $PO_4^{3-}$ surface-modified of $Fe_3O_4$ magnetic particles used to adsorb calcium oxalate. FIG. 5A is a diagram showing pure substance powder of Calcium oxalate. FIG. 5B is a diagram showing the magnetic particles formed by $Fe_3O_4$ added in surface-modified $PO_4^{3-}$ groups. The magnetic particles adsorb onto the Calcium oxalate. FIG. 5C is a diagram showing the magnetic particles and the Calcium oxalate attracted by an external magnet. Please refer to FIG. 6 showing a diagram of the magnetic particles 50 adsorb onto Calcium oxalate 110. It means that if the urine sample is displayed with Calcium or Magnesium in urinary crystals, such as calcium oxalate, the urinary crystals can be separated by attaching to the magnetic particles 50 and adding an external magnetic field.

Figure 7:
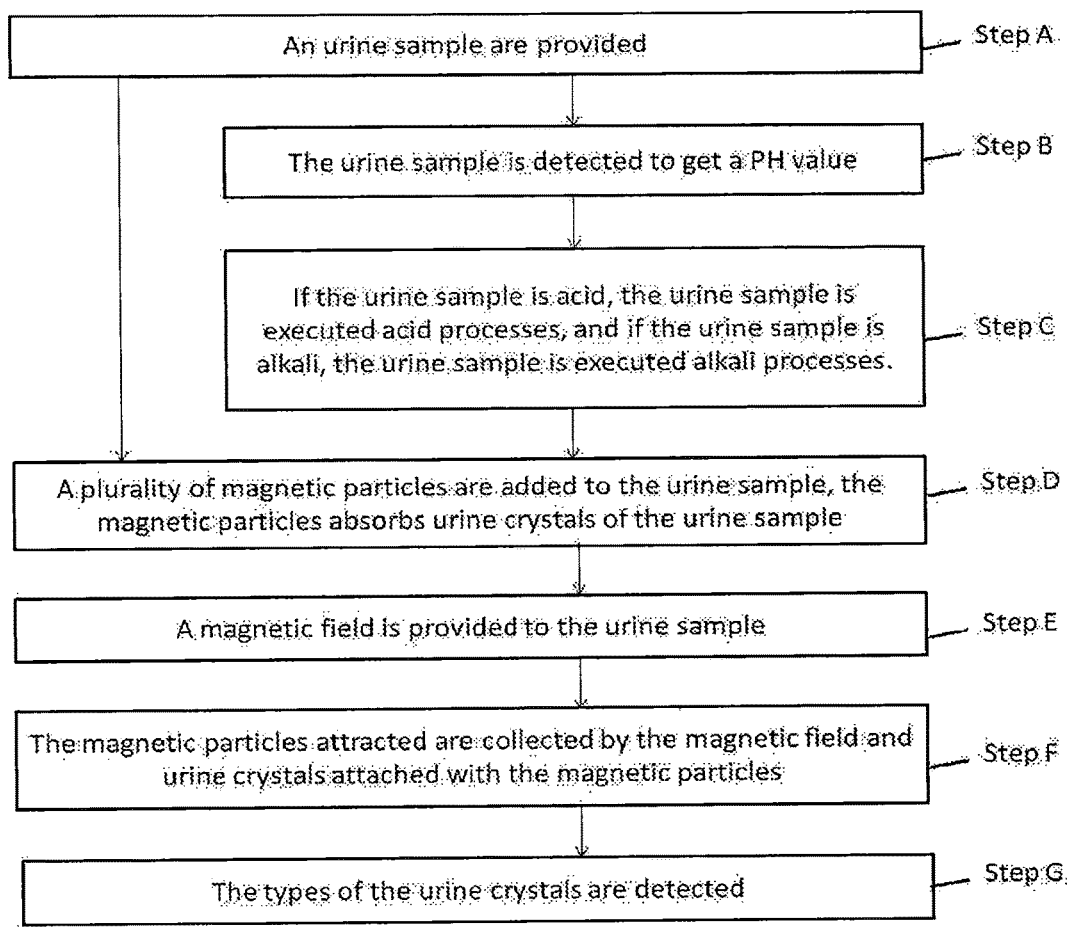
FIG. 7 shows a flow chart of the urinary crystal detection method.

Otherwise, the present invention provides an urinary crystal detection method. Please refer to FIG. 7 showing a flow chart of the urinary crystal detection method and the steps are as following:

Step A. An urine sample are provided. In an embodiment, the amount of the urine sample is 1-5 ml from a patient's urine.

Step B. The urine sample is detected to get a pH value.

Step B. The urine sample is detected to get a pH value.

Step C, Processes are executed according to the pH value. If the pH value of urine sample 10 is less than 7, the urine sample is executed acid processes. And the pH value of urine sample 10 is larger than 7, the urine sample is executed alkali processes. In an embodiment, the acid processes comprise a step of adding 5%~15% acetic acid to the urine sample, and the alkali processes comprise a step of adding 5%~15% NaOH to the urine sample. After pretreatments, the urine sample Ruins urinary crystals, which is not limited herein.

Step D. A plurality of magnetic particles are added into the urine sample, the magnetic particles adsorbs urinary crystals of the urine sample.

Step E. A magnetic field is provided to the urine sample. In an embodiment, the urine sample is provided an external magnet to attract the magnetic particles.

Step F. The magnetic particles attracted are collect by the magnetic field.

Step G. The types of the urinary crystals are detected, and comparing the types of urinary crystals with a component information from a database to receive a result of the urinary calculus.

In an embodiment, a Raman signal of the urinary crystals is detected to get an analyzing result used to determine the type of the urinary crystals, and the peak characteristics of the Raman signals are compared with a component information from a database, wherein the component information is a plurality of reference peak characteristics from different urinary crystals related to a plurality of urinary calculus. It can receive a result of the urinary calculus which the reference peak characteristics is similar as the Raman signal.

The urinary crystal detection method can be executed step by step (above Step A to Step G orderly), and also be executed from step A and then directly performing step D. Each step can be adjusted according to different cases, which is not limited herein.

Figure 8A:
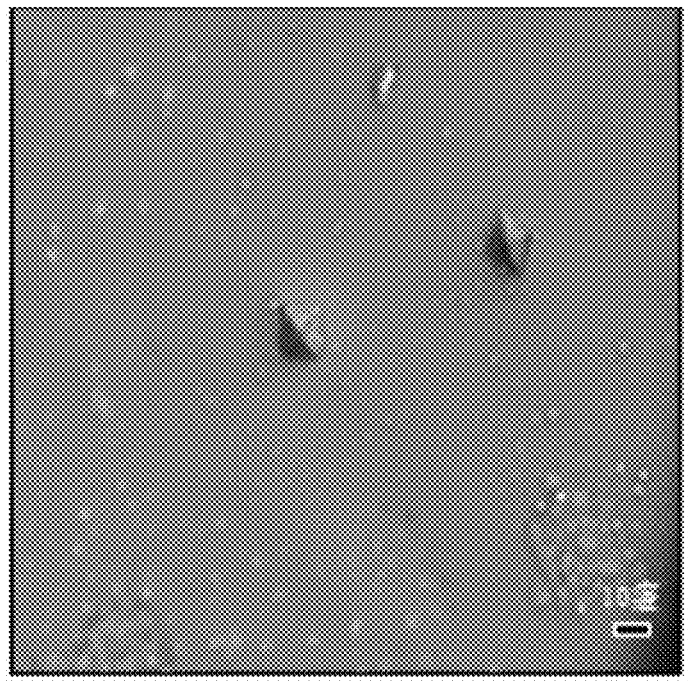
FIG. 8A is a diagram of urinary crystals under the microscope, and the status of the urinary crystals is calcium oxalate dihydrate (COD).
Figure 8B:
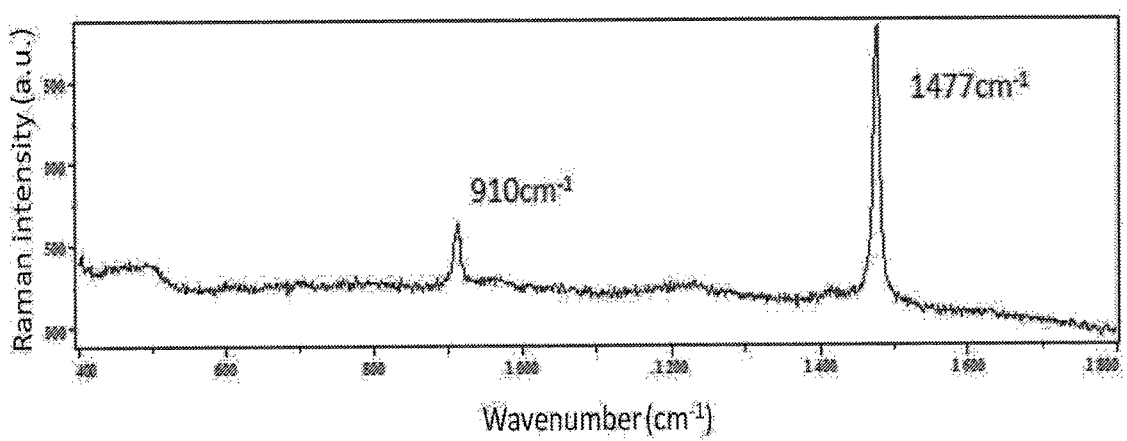
FIG. 8B is a diagram of Raman signals of the COD.

As above embodiment, please refer to FIG. 8A and FIG. 8B showing an urinary calculus patient's analyzing results from the urinary crystal detection system and method of the invention. FIG. 8A is a diagram of urinary crystals under a microscope, and the status of the urinary crystals is calcium oxalate dihydrate (COD). FIG. 8B is a diagram of Raman signals from COD. In FIG. 8B, it can show that the peak characteristics of Raman signals in COD are 910 (cm$^{-1}$) and 1477 (cm$^{-1}$).

Figure 9A:
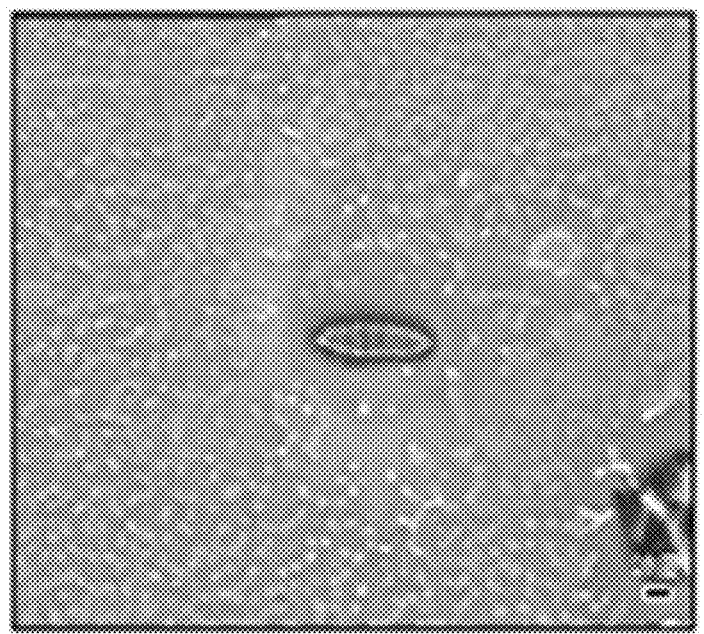
FIG. 9A is a diagram of urinary crystals under the microscope, and the status of the urinary crystals is hydroxyapatite (HAP).
Figure 9B:
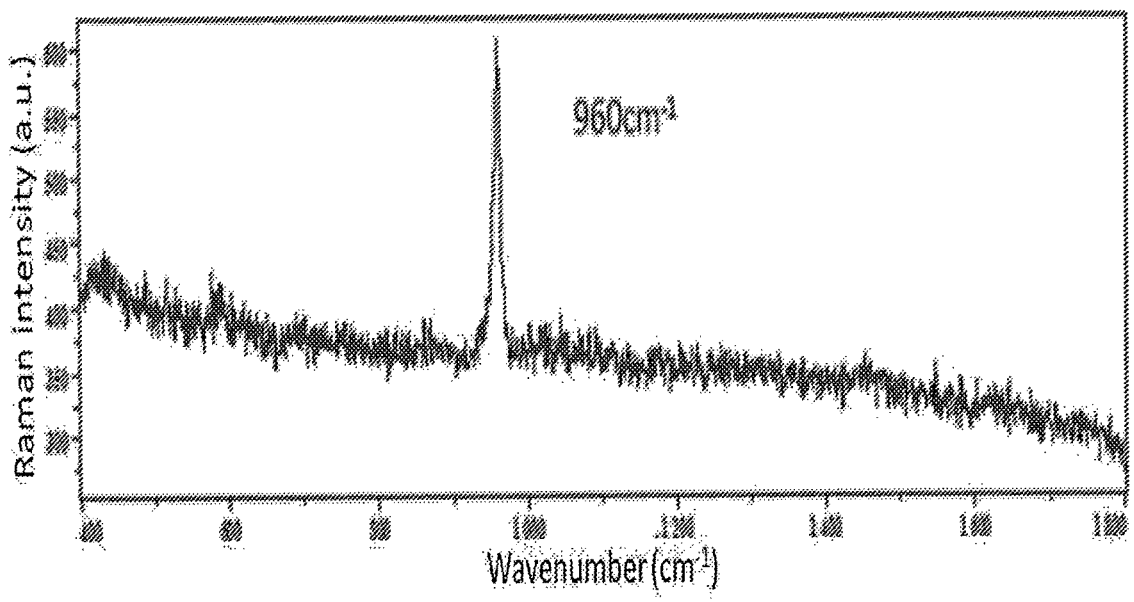
FIG. 9B is a diagram of Raman signals of the HAP.

In another embodiment of the present invention, please refer to FIG. 9A and FIG. 9B showing another urinary calculus patient's analyzing results from the urinary crystal detection system and method of the invention. FIG. 9A is a diagram of urinary crystals under the microscope, and the status of the urinary crystals is hydroxyapatite (HAP). FIG. 9B is is a diagram of Raman signals of the HAP. In FIG. 9B, it can show that the peak characteristic of Raman signals in HAP is 960 (cm$^{-1}$).

The urinary crystal detection system and method of the invention can be used to detect all kinds of urinary crystals, and construct a database via the analyzing results and further to be the reference for comparison afterwards. For example, in an embodiment of the invention, a database is constructed by Raman signals from all kinds of urinary crystals, as shown in table 1, but which is not limited herein.

TABLE 1 the database of Raman signals.

| Urinary crystal/calculus | peak characteristics of Raman signals (cm$^{-1}$) |
| --- | --- |
| COM (calcium oxalate monohydrate) | 895 ` 1462 |
| COD (calcium oxalate dihydrate) | 910 ` 1477 |
| DCPD (dicalcium phosphate dihydrate) | 986 |
| HAP(hydroxyapatite) | 960 |
| Uric acid | 623 ` 996 ` 1036 |
| Struvite (magnesium ammonium phosphate) | 563 ` 944 |
| Cystine | 498 |

In another embodiment, an auto-fluorescence signal of the urinary crystals is detected to get an analyzing result by a fluorescence spectroscopy unit. The auto-fluorescence happening is because of organic matter, protein or other substances doped in the formation of the crystallization process, and the crystalline surface also may adsorb protein. Auto-fluorescence signal may be excited from different excitation bands, from UV to near infrared light. It is presumed that the urinary crystals may aggregate to form the urinary stones. In the invention, we use different wavelengths of light to excite crystallization to produce different wavelengths of auto-fluorescence, and determine the composition of crystallization (or crystalline surface) organic matter. It is presumed whether the urinary crystals have the risk to aggregate stones.

In sum, the urinary crystal detection system and method of the invention can efficiently collect and detect the urinary crystals in the urine. The urine of an urinary calculus patient generally has urinary crystals. Custom made magnetic nanoparticles and an external magnetic field can be used to collect and separate urinary crystals/micro urine stones from other substances in urine. The types of urinary crystals can be determined by the Raman signals. Early detection can be achieved for urinary calculus patients by measuring their urinary crystal. For emergency cases, if the patient has urinary calculus symptoms, this invention can also provide real-time diagnostic efficacy. The invention has the advantages of assisting clinical examination to determine the type of the urinary crystals that may be hard to determine. It is more accurate, more specific, and can assist clinicians to provide individual treatment for the patients according to different types of urinary crystals. It is also convenient to keep tracking and monitoring the patients after the urine stone surgery and to reduce the relapse rate.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. An urinary crystal detection method, comprising steps:
   providing a urine sample from a patient;
   adding a plurality of magnetic particles into the urine sample, the magnetic particles attaching to a plurality of urine crystals of the urine sample, wherein the magnetic particles are formed as a core, which is coated with gelatin, and the surfaces of the magnetic particles are modified by PO(OH)$_2$ or PO$_4^{3-}$ groups to attach the urinary crystals with Ca or Mg;
   providing a magnetic field to attract the magnetic particles by a magnetic separating device, and collecting the urinary crystals which are absorbed by the magnetic particles;
   analyzing a Raman signal of the urinary crystals by a microscopic Raman spectroscopy unit;
   comparing the peak characteristics of the Raman signal with a component information from a database, wherein the component information is a plurality of reference peak characteristics from different urinary crystals related to a plurality of urinary calculus; and
   receiving a result of the urinary calculus which the reference peak characteristics is similar as the Raman signal.

2. The urinary crystal detection method of claim 1, wherein the component of the magnetic particles are formed by Fe$_3$O$_4$ coated with gelatin or PSMA.

3. The urinary crystal detection method of claim 1, wherein the size of the magnetic particle is 5 nm~200 nm.

4. The urinary crystal detection method of claim 1, wherein the gelatin are modified by FITC.

5. The urinary crystal detection method of claim 1, wherein the magnetic separating device is a magnet or a magnetite.

6. The urinary crystal detection method of claim 1, wherein the steps further comprise processing the urine sample before the step of adding the magnetic particles into the urine sample, includes:
   detecting the urine sample to get a pH value; and
   executing processes according to the pH value, if the pH value of urine sample is less than 7, the urine sample is executed an acid processes; if the pH value of urine sample 10 is larger than 7, the urine sample is executed an alkali processes.

7. The urinary crystal detection method of claim 6, wherein the acid processes comprise a step of adding 5%~15% acetic acid to the urine sample.

8. The urinary crystal detection method of claim 6, wherein the alkali processes comprise a step of adding 5%~15% NaOH to the urine sample.

9. The urinary crystal detection method of claim 1, wherein the steps further comprises analyzing an auto-fluorescence signal of the urinary crystals by a fluorescence spectroscopy unit.

10. The urinary crystal detection method of claim 1, wherein the surfaces of the magnetic particles are modified by a plurality of fluorescent molecules.

11. The urinary crystal detection method of claim 10, wherein the fluorescent molecules are PAR or CV.

12. The urinary crystal detection method of claim 11, wherein the steps further comprises analyzing a fluorescence signal of the fluorescent molecules by a fluorescence spectroscopy unit.

* * * * *